United States Patent
Gerdts et al.

(10) Patent No.: US 6,592,549 B2
(45) Date of Patent: Jul. 15, 2003

(54) RAPID EXCHANGE STENT DELIVERY SYSTEM AND ASSOCIATED COMPONENTS

(75) Inventors: Michael Gerdts, Big Lake, MN (US); Mary Bronson, Elk River, MN (US); August Powell, Zimmerman, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 36 days.

(21) Appl. No.: 09/808,626

(22) Filed: Mar. 14, 2001

(65) Prior Publication Data

US 2002/0133118 A1 Sep. 19, 2002

(51) Int. Cl.$^7$ ............................................. A61M 29/00
(52) U.S. Cl. ............................ 604/103.04; 604/96.01; 606/195; 623/1.12
(58) Field of Search ......................... 604/103.04, 96, 604/97, 98, 99, 100, 101; 606/191, 194, 195; 623/1.11, 1.12

(56) References Cited

U.S. PATENT DOCUMENTS

| | | | |
|---|---|---|---|
| 4,655,771 A | | 4/1987 | Wallsten .......................... 623/1 |
| 4,848,343 A | | 7/1989 | Wallsten et al. ............. 128/343 |
| 4,990,151 A | | 2/1991 | Wallsten ...................... 606/108 |
| 5,026,377 A | | 6/1991 | Burton et al. ................ 606/108 |
| 5,324,269 A | | 6/1994 | Miraki .......................... 604/160 |
| 5,360,401 A | * | 11/1994 | Turnland ....................... 604/96 |
| 5,389,087 A | | 2/1995 | Miraki ......................... 604/247 |
| 5,458,605 A | * | 10/1995 | Klemm ........................ 606/108 |
| 5,484,444 A | | 1/1996 | Braunschweiler et al. ... 606/108 |
| 5,507,768 A | * | 4/1996 | Lau et al. ..................... 606/198 |
| 5,533,968 A | * | 7/1996 | Muni et al. ..................... 604/96 |
| 5,690,644 A | * | 11/1997 | Yurek et al. ................. 606/108 |
| 5,709,703 A | | 1/1998 | Lukie et al. ................. 606/198 |
| 5,743,874 A | | 4/1998 | Fischell et al. ............... 604/96 |
| 5,782,855 A | * | 7/1998 | Lau et al. ..................... 606/194 |
| 5,843,028 A | | 12/1998 | Weaver et al. ................. 604/54 |
| 5,921,971 A | | 7/1999 | Agro et al. .................. 604/280 |
| 5,980,533 A | * | 11/1999 | Holman ........................ 606/108 |
| 6,007,522 A | | 12/1999 | Agro et al. .................. 604/264 |
| 6,059,752 A | * | 5/2000 | Segal .......................... 604/107 |
| 6,077,295 A | * | 6/2000 | Limon et al. ................... 623/1 |
| 6,113,607 A | * | 9/2000 | Lau et al. ..................... 606/108 |

FOREIGN PATENT DOCUMENTS

WO    WO 00/69498    11/2000

* cited by examiner

Primary Examiner—James Hook
(74) Attorney, Agent, or Firm—Crompton, Seager & Tufte, LLC

(57) ABSTRACT

A rapid exchange stent delivery catheter which includes an inner tubular member and an outer tubular member slidably disposed thereon. The inner tubular member and the outer tubular member have rapid exchange type guide wire openings. The guide wire opening of the outer tubular member is preferably shorter in length than the guide wire opening of the inner tubular member to protect the inner workings of the catheter. The outer tubular member may include a guide wire access sleeve having a guide wire ramp extending into the guide wire lumen of the inner tubular member. The guide wire sleeve may be a separate component from the remainder of the outer tubular member to facilitate efficient manufacture.

12 Claims, 3 Drawing Sheets

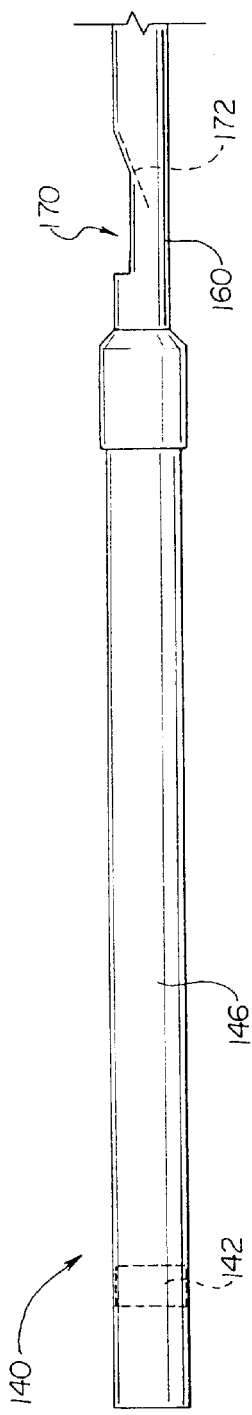
Fig. 3
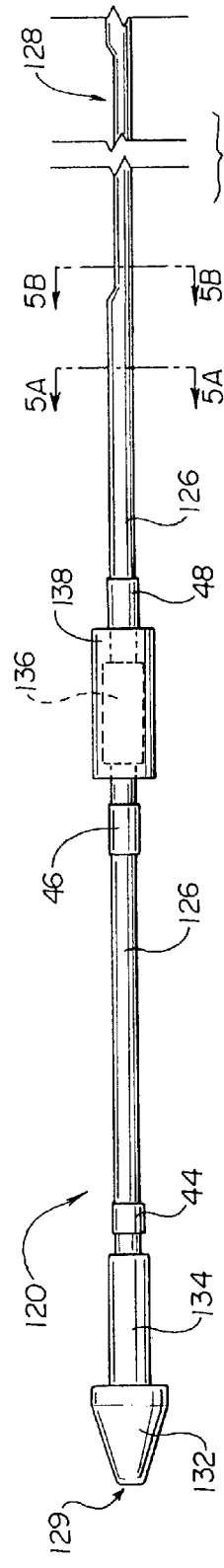
Fig. 4
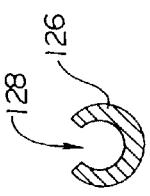
Fig. 5A    Fig. 5B
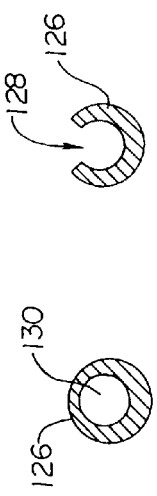
Fig. 6

RAPID EXCHANGE STENT DELIVERY SYSTEM AND ASSOCIATED COMPONENTS

FIELD OF THE INVENTION

The present invention generally relates to stent delivery catheters, such as biliary stent delivery catheters. More specifically, the present invention relates to rapid exchange type stent delivery catheters for delivering a self-expanding stent to a bodily lumen, such as the biliary tract.

BACKGROUND OF THE INVENTION

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with a guidewire under fluoroscopy. A wide variety of catheters are known for treatment of such targeted anatomical regions. Examples of biliary catheters are disclosed in U.S. Pat. No. 5,921,971 to Agro et al. atad PCT International Publication No. 00/69498 to De Toledo et al., the disclosures of which are hereby incorporated by reference.

Agro et al. '971 discloses a catheter for use in biliary procedures, wherein the catheter includes a shaft having a proximal end and a distal end. A guidewire lumen extends through the shaft from a proximal guidewire port located proximal of the distal end of the shaft, to a distal guidewire port located at the distal end of the shaft. The shaft may also include a slot or channel extending from a proximal end of the shaft to the proximal guidewire port. Catheters incorporating such a guidewire opening and channel are often referred to as rapid exchange or single operator exchange type biliary catheters.

De Toledo et al. '498 discloses single operator drainage catheter delivery system including a guide member having a guidewire lumen extending through a distal portion thereof, with a proximal guidewire port located distal of the proximal end. A placement catheter is disposed over the guide member has a catheter lumen extending through a distal portion thereof, with a proximal guidewire port located distal of the proximal end. Locating the proximal guidewire ports as such allows the delivery system to be used by a single person with a shorter guidewire. A drainage catheter (a.k.a. a plastic stent) is disposed about the guide member distal of the placement catheter. The drainage catheter delivery system preferably includes a means for releasably connecting the placement catheter to the drainage catheter, wherein the releasable connecting means disconnects the drainage catheter upon displacement of the guide member. However, De Toledo et al. '498 does not disclose a rapid exchange biliary catheter system for the delivery of a metallic self-expanding stent, which requires a retractable sheath.

U.S. Pat. No. 5,484,444 to Braunschweiler et al., and U.S. Pat. No. 5,709,703 to Lukic et al. disclose a stent delivery device which has an elongated sheath with a self-expandable stent placed in contracted condition within the distal area of the sheath. An elongated core is arranged in the sheath for longitudinal motion relative to the sheath to facilitate stent delivery. However, Braunschweiler et al. '444 and Lukic et al.'703 do not provide a rapid exchange feature as in De Toledo et al. '498.

U.S. Pat. No. 5,743,874 to Fischell et al. discloses a catheter capable of performing balloon angioplasty followed by delivery of a self-expanding stent. The catheter includes an outer sheath which may be pulled back to deploy the self-expanding stent. In one embodiment, the catheter includes a guide wire entry port located just proximal of the stent to permit rapid exchange capability. To provide the guide wire entry port, Fischell et al. '874 provides a sloped plug disposed in the inner tube and an elongate side opening in the outer sheath. The elongate side opening in the outer sheath is necessary to permit retraction of the outer sheath for stent deployment. By providing such a long side opening, a major portion of the inner workings of the catheter are exposed to bodily fluids and interference from other devices, which may compromise performance of the stent delivery catheter. This undesirable feature, in addition to others not specifically mentioned herein, leaves a need for an improved rapid exchange stent delivery catheter.

SUMMARY OF THE INVENTION

The present invention provides an improved rapid exchange catheter system for the delivery of a self-expanding stent to a bodily lumen (e.g., biliary tract, blood vessel, etc.), such as a metallic biliary stent commercially available from Boston Scientific Corporation under the trade name Wallstent™. In an exemplary embodiment, the rapid exchange stent delivery catheter includes an inner tubular member and an outer tubular member slidably disposed thereon. The inner tubular member has a guide wire lumen with a proximal rapid exchange type guide wire opening. The outer tubular member also has a rapid exchange type guide wire opening that is preferably shorter than the guide wire lumen of the inner tubular member in order to protect the inner workings of the catheter from bodily fluids and other devices.

The outer tubular member may include a guide wire access sleeve in which the guide wire opening is disposed. The guide wire access sleeve has a guide wire ramp extending into the guide wire lumen of the inner tubular member. The guide wire sleeve may be a separate component from the remainder of the outer tubular member to facilitate efficient manufacture.

BRIEF DESCRIPTION OF THE DRAWINGS

FIG. 3 is a plan view of a distal portion of the outer tubular member of the rapid exchange catheter illustrated in FIG. 1;

FIG. 4 is a plan view of an inner tubular member of the rapid exchange catheter illustrated in FIG. 1;

FIGS. 5A and 5B are cross-sectional views taken along lines 5A—5A and 5B—5B, respectively, in FIG. 4;

FIG. 6 is a plan view of a self-expanding metallic stent suitable for delivery by the rapid exchange catheter illustrated in FIG. 1;

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention. Those skilled in the art will recognize that the dimensions and materials discussed herein are merely exemplary and are not intended to limit the scope of the present invention.

Figure 1:
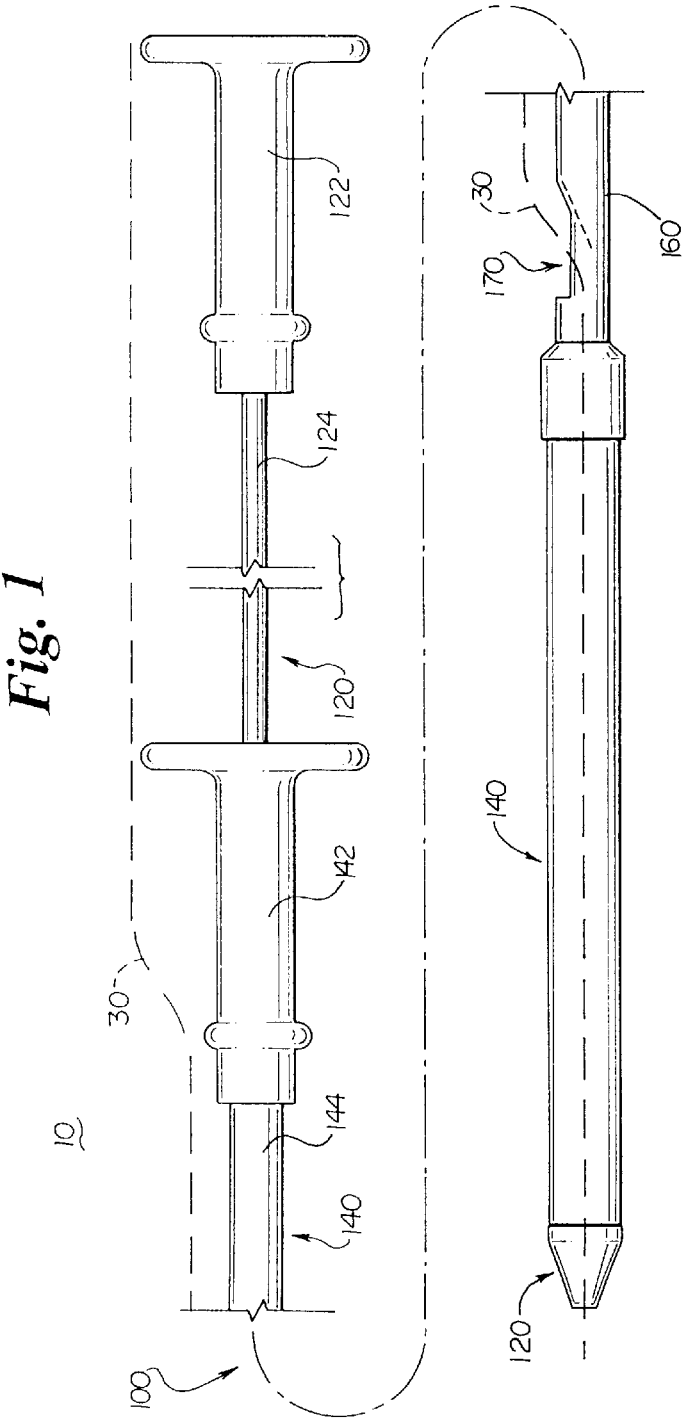
FIG. 1 is a plan view of a rapid exchange stent delivery catheter system in accordance with an exemplary embodiment of the present invention, shown in the delivery state.
Figure 2:
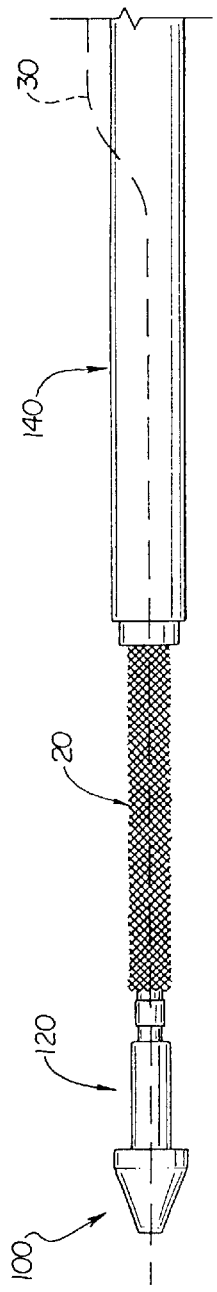
FIG. 2 is a plan view of a distal portion of the rapid exchange stent delivery catheter system illustrated in FIG. 1, shown in the deployment state.

Refer now to FIGS. 1 and 2 which illustrate plan views of a rapid exchange stent delivery catheter system 10 in accordance with an embodiment of the present invention. The rapid exchange stent delivery catheter system 10 includes a rapid exchange catheter 100 which is advanced over a guide wire 30 (shown in phantom) to deliver and deploy a self-expanding stent 20 in a bodily lumen.

The rapid exchange stent delivery catheter system 10 is suitable for biliary applications and intravascular applications. In biliary applications, the rapid exchange stent delivery catheter system 10 is sized to fit within an endoscope (not shown) and to navigate to the desired site in the biliary tract. In vascular applications, the rapid exchange stent delivery catheter system 10 is sized to fit within an introducer sheath (not shown) and/or a guide catheter (not shown) to navigate to the desired vascular site.

The rapid exchange stent delivery catheter 100 includes an inner tubular member 120 slidably disposed in an outer tubular member 140. The outer tubular member 140 includes a lumen (not visible) extending therethrough to slidably accommodate the inner tubular member 120. The inner tubular member 120 includes a guide wire lumen 130 extending through a distal portion thereof to accommodate the guide wire 30.

To provide rapid exchange capability for the rapid exchange stent delivery catheter 100, the guide wire 30 exits through a guide wire opening 170 in the outer tubular member 140 as will be discussed in greater detail with reference to FIGS. 3, 7A and 7B. The guide wire 30 extends through a relatively short guide wire lumen and enters through a distal guide wire opening in the inner tubular member 129, as will be discussed in greater detail with reference to FIGS. 4, 5A and 5B. In practice, the device 100 may be inserted over the guide wire 30 from the tip end first.

A proximal handle 122 is connected to a proximal portion 124 of the inner tubular member 120. Similarly, a distal handle 142 is connected to a proximal portion 144 of the outer tubular member 140. The distal handle 142 may be longitudinally displaced relative to the proximal handle 122 to selectively expose or cover the self-expanding stent 20, which is disposed about a distal portion of the inner tubular member 120. In FIG. 1, the distal handle 142 has been longitudinally displaced in the distal direction relative to proximal handle 122 such that the outer tubular member 140 covers the self-expanding stent 20. In FIG. 2, the distal handle 142 has been longitudinally displaced in the proximal direction relative to proximal handle 122 to retract the outer tubular member 140 relative to the inner tubular member 120 to expose and deploy the self-expanding stent 20.

With additional reference to FIG. 3, the outer tubular member 140 includes, from the proximal end to the distal end, a proximal portion 144, a main outer portion (not visible) a guide wire sleeve 160 and a distal outer portion 146. The proximal end of the proximal outer portion 144 is connected to the distal handle 142. The distal handle 142 may be injection molded over the proximal outer portion 144. The distal end of the proximal outer portion 144 is connected to the proximal end of the main outer portion (not visible). The distal end of the main outer portion (not visible) is connected to the proximal end of the guide wire sleeve 160, and the distal end of the guide wire sleeve 160 is connected to the proximal end of the distal outer portion 146. The various portions of the outer tubular member 140 may be connected by adhesive, by thermal means or by any other suitable means known to those skilled in the art.

The proximal outer portion 144 may be formed of PEBAX, having a length of approximately 8.0 inches (20.3 cm), an outside profile of approximately 0.120 inches (9F) (0.30 cm), and an inside diameter of approximately 0.083 inches (0.21 cm). The guide wire sleeve 160 is discussed in greater detail with reference to FIGS. 7A and 7B. The main outer portion (not visible) may be formed of PEBAX/wire braid/PTFE composite, having a length of approximately 55.0 inches (0.140 cm), an outside profile of approximately 6F (0.079 inches), and an inside diameter of approximately 0.057 inches (0.145 cm). The distal outer portion 146 may be formed of PEBAX/wire braid/PTFE composite, having a length of approximately 10.6 inches (27 cm), an outside profile of approximately 8F 0.105 inches, and an inside diameter of approximately 0.090 inches (0.229 cm).

A radiopaque marker band 42 may be disposed adjacent the distal end of the distal outer portion 146 to facilitate radiographic placement of the catheter 100 and to radiographically indicate the position of the outer tubular member 140 relative to the inner tubular member 120 to aid in deploying the self-expanding stent 20.

With additional reference to FIGS. 4, 5A and 5B, the inner tubular member 120 includes a distal inner portion 126 connected to the distal end of the proximal inner portion 124. The proximal inner portion 124 and the distal inner portion 126 are essentially the same, except the proximal inner portion 124 is reinforced with a SST hypotube. The inner portions 124/126 may be formed of PEEK, having a length of approximately 88.6 inches (225 cm), an outside profile of approximately 0.052 inches (0.13 cm), and an inside diameter of approximately 0.037 inches (0.094 cm). A jacket formed of LDPE, having a length of approximately 5.9 inches (15 cm), an outside profile of approximately 0.80 inches (0.020 cm), and an inside diameter of approximately 0.055 inches (0.14 cm) may be disposed about the inner member 120 to consume the clearance between the inner member 120 and the outer member 140 proximal of the stent 20 to prevent kinking. The various portions of the inner tubular member 120 may be connected by adhesive, by thermal means or by any other suitable means known to those skilled in the art.

A distal head 132 is connected to the distal end of the distal inner portion 126 to limit distal displacement of the outer tubular member 140. A distal bond region 134 is disposed immediately proximal of the distal head 132. A holding sleeve 136 and a stent cup 138 prevent slippage of the stent 20. Radiopaque marker bands 44/48 are disposed on the distal inner portion 126 and are separated by a distance approximately equal to the length of the stent 20. The distal outer portion 146 of the outer tubular member 140 contains the self-expanding stent 20 during delivery.

The distal inner portion 126 includes a proximal guide wire opening 128 and a distal guide wire opening 129. A guide wire lumen 130 extends between the proximal guide wire opening 128 and the distal guide wire opening 129 to accommodate the guide wire 30 therein. The proximal guide wire opening 128 has a length which is greater than the length of the guide wire opening 170 of the guide wire sleeve 160. The length of the proximal guide wire opening 128 is sufficient to allow longitudinal displacement of the outer tubular member 140 relative to the inner tubular member 120 to permit full exposure and deployment of the self-expanding stent 20. The length of the proximal guide wire opening 128 is preferably slightly longer than the length of the constrained portion of the stent 20 to avoid wedging the guide wire 30 between the inner tubular member 120 and the outer tubular member 140 prior to full deployment of the stent 20.

The guide wire lumen 130 may be eccentrically positioned in the distal inner portion 126 as seen in FIGS. 5A and 5B. For example, the upper wall may have a thickness of approximately 0.003 inches and the lower wall may have a thickness of approximately 0.011 inches. The upper thinner wall portion may be removed (skived) to define the proximal guide wire opening 128. By removing only the thin-walled portion of the distal inner portion 126, the column strength of the inner tubular member 120 is not significantly compromised.

A solid mandrel (not shown) may be inserted into the proximal lumen (not visible) of the inner tubular member 120 proximal of the guide wire opening 128 for improved column strength. The solid mandrel may be formed of stainless steel having an outside diameter of approximately 0.030 inches with a tapered end. A stainless steel hypotube (not shown) having an outside diameter of approximately 0.079 inches may be disposed about the proximal inner portion 124 for added column strength and durability. The proximal handle 122 may be injection molded over the proximal end of the hypotube and the proximal end of the proximal inner portion 124.

A distal radiopaque marker 44 is disposed on the distal inner portion 126 to radiographically mark the distal end of the stent 20. A proximal radiopaque marker 48 is disposed on the distal inner portion 126 to radiographically mark the proximal end of the stent 20. A mid radiopaque marker 46 is disposed on the distal inner portion 126 distal of the holding sleeve 138 to radiographically facilitate deployment of the stent 20.

With reference to FIG. 6, the stent 20 may comprise any self-expanding stent suitable for biliary or intravascular applications. For example, in biliary applications, the self-expanding stent 20 may comprise a metallic stent commercially available from Boston Scientific Corporation under the trade name Wallstent ™.

Figure 7A:
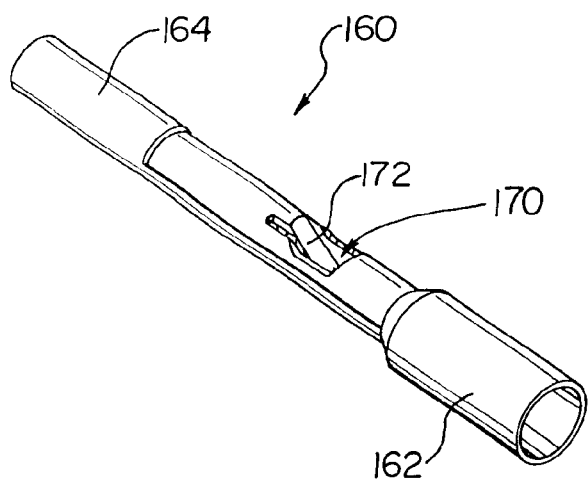
FIG. 7A is an isometric view of a guide wire sleeve of the outer tubular member illustrated in FIG. 3.
Figure 7B:
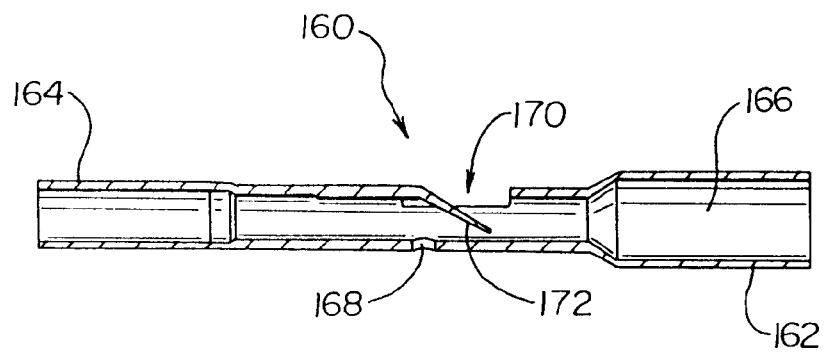
FIG. 7B is a longitudinal sectional view of the guide wire sleeve illustrated in FIG. 7A.

With reference to FIGS. 7A and 7B, the guide wire sleeve 160 includes a proximal portion 164, a distal portion 162 and a lumen 166 extending therethrough. The distal portion 162 is flared to fit over and be connect to the distal outer portion 146. The proximal portion 164 is sized to fit within and be connected to the main outer portion.

A guide wire opening 170 extends through the exterior wall of the guide wire sleeve 160. A ramp 172 extends from the exterior wall into the lumen 166. When assembled, the ramp 172 extends through the proximal guide wire opening 128 of the inner tubular member 120 and into the guide wire lumen 130. The ramp 172 is moveable within the proximal guide wire opening 128 to facilitate a smooth transition of the guide wire 30 from the guide wire lumen 130 to exterior of the catheter 100, regardless of the position of the outer tubular member 140 relative to the inner tubular member 120.

The guide wire sleeve 160 may have a length of approximately 1.0 inch, a distal outside diameter of approximately 0.122 inches, a proximal outside diameter of approximately 0.087 inches, a distal inside diameter of approximately 0.107 inches, and a proximal inside diameter of approximately 0.070 inches. The ramp 172 may be an intrigal extension of the exterior wall of the guide wire sleeve 160 and may have a length of approximately 0.090 inches and a width of approximately 0.50 inches. The ramp 172 may extend into the lumen 166 at an angle of approximately 30 degrees to a point approximately 0.14 inches away from the opposite wall.

The guide wire sleeve 160 may be an intrigal part of the outer tubular member 140 but is preferably a separately manufactured component. For example, the guide wire sleeve 160 may be formed of injection molded nylon or polypropylene. If the guide wire sleeve 160 is injection molded, manufacturing artifacts such as hole 168 may be filled or removed depending on the particular application. By manufacturing the guide wire sleeve 160 separately, more manufacturing flexibility and efficiency are achieved. For example, the guide wire sleeve 160 may be made of a material that is not melt sensitive or that is readily bonded to facilitate connection to other catheter components using adhesive or thermal means. In addition, the guide wire sleeve 160 may be inspected prior entering the production floor to eliminate non-conforming parts and increase efficiency. Further, the dimensions may be controlled better to provide greater consistency at bond sites. These and other advantages not specifically mentioned herein may be obtained by manufacturing the guide wire sleeve 160 as a separate component, but such is not essential to the present invention.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A rapid exchange stent delivery catheter for delivering a self-expandable stent over a guide wire to a bodily lumen, the catheter comprising:

an inner tubular member having a proximal end, a distal end, a stent holding portion located adjacent the distal end of the inner member, and a guide wire lumen extending from a proximal guide wire opening disposed distal of the proximal end of the inner member to a distal guide wire opening disposed at the distal end of the inner member, wherein the proximal guide wire opening has a length;

an outer tubular member slidably disposed about the inner member, the outer member having a proximal end, a main portion, a distal end, and a guide wire opening disposed distal of the proximal end of the outer member, wherein the guide wire opening of the outer member has a length that is shorter than the length of the proximal guide wire opening of the inner member, wherein the outer member is sized to cover a major portion of the proximal guidewire opening of the inner member.

2. A rapid exchange stent delivery catheter for delivering a self-expandable stent over a guide wire to a bodily lumen, the catheter comprising:

an inner tubular member having a proximal end, a distal end, a stent holding portion located adjacent the distal end of the inner member, and a guide wire lumen extending from a proximal guide wire opening disposed distal of the proximal end of the inner member to a distal guide wire opening disposed at the distal end of the inner member, wherein the proximal guide wire opening has a length;

an outer tubular member slidably disposed about the inner member, the outer member having a proximal end, a main portion, a distal end, and a guide wire opening disposed distal of the proximal end of the outer member, wherein the guide wire opening of the outer member has a length that is shorter than the length of the proximal guide wire opening of the inner member; and wherein the outer tubular member includes a guide wire access sleeve in which the guide wire opening is disposed, the guide wire access sleeve having a guide wire ramp extending into the guide wire lumen of the inner tubular member.

3. A rapid exchange stent delivery catheter as in claim 2, wherein the guide wire access sleeve has an exterior wall, and wherein the ramp extends from the exterior wall, through the guide wire opening of the outer tubular member and the proximal guide wire opening of the inner tubular member, and into the guide wire lumen of the inner tubular member.

4. A rapid exchange stent delivery catheter as in claim 3, wherein the ramp is an integral extension of the exterior wall.

5. A rapid exchange stent delivery catheter as in claim 4, wherein the outer tubular member includes a proximal outer portion and a distal outer portion with the guide wire sleeve connected therebetween.

6. A rapid exchange stent delivery catheter as in claim 5, wherein the guide wire sleeve is a separate component from the proximal outer portion and the distal outer portion of the outer tubular member.

7. A rapid exchange catheter, comprising:

an inner tubular member having a proximal end, a distal end, and a guide wire lumen extending from a proximal guide wire opening disposed distal of the proximal end of the inner member to a distal guide wire opening disposed at the distal end of the inner member;

an outer tubular member slidably disposed about the inner member, the outer member having a proximal end, a main portion, a distal end, and a guide wire access sleeve disposed distal of the proximal end of the outer member, the guide wire access sleeve having a guide wire opening and a guide wire ramp extending into the guide wire lumen of the inner tubular member.

8. A rapid exchange catheter as in claim 7, wherein the guide wire opening of the outer member has a length that is shorter than a length of the proximal guide wire opening of the inner member.

9. A rapid exchange catheter as in claim 8, wherein the guide wire access sleeve has an exterior wall, and wherein the ramp extends from the exterior wall, through the guide wire opening of the outer tubular member and the proximal guide wire opening of the inner tubular member, and into the guide wire lumen of the inner tubular member.

10. A rapid exchange catheter as in claim 9, wherein the ramp is an integral extension of the exterior wall.

11. A rapid exchange catheter as in claim 10, wherein the outer tubular member includes a proximal outer portion and a distal outer portion with the guide wire sleeve connected therebetween.

12. A rapid exchange catheter as in claim 11, wherein the guide wire sleeve is a separate component from the proximal outer portion and the distal outer portion of the outer tubular member.

* * * * *